United States Patent [19]

Hinge

[11] 4,312,370
[45] Jan. 26, 1982

[54] TOOTHPICK

[76] Inventor: George Hinge, 621 Jacobs Rd., Youngstown, Ohio 44505

[21] Appl. No.: 149,508

[22] Filed: May 13, 1980

[51] Int. Cl.³ .......................................... A61C 15/00
[52] U.S. Cl. .................................. 132/93; 206/380
[58] Field of Search ...................... 206/380; 132/89, 93

[56] References Cited
U.S. PATENT DOCUMENTS

| | | | |
|---|---|---|---|
| 2,035,425 | 3/1936 | Doll | 132/93 |
| 2,760,628 | 8/1956 | Briggs | 132/93 |
| 3,130,885 | 4/1964 | Fleming | 132/93 |
| 3,438,486 | 4/1969 | Pinkas | 132/93 |
| 3,511,249 | 5/1970 | Baitz | 132/93 |
| 3,779,256 | 12/1973 | Maloney et al. | 132/93 |

Primary Examiner—William T. Dixson, Jr.
Attorney, Agent, or Firm—Harpman & Harpman

[57] ABSTRACT

A toothpick comprises an elongated section of thin corrugated plastic material such as synthetic resin, the opposite ends of the material are curved so that one end defines a projecting point. The corrugations run longitudinally so that the projecting point is relatively stiff. The plastic material is quite thin so as to enable the several parts of the toothpick to be moved between adjacent teeth to free food therefrom.

6 Claims, 2 Drawing Figures

TOOTHPICK

BACKGROUND OF THE INVENTION

1. Field of the Invention

This invention relates to toothpicks and similar devices which can be moved relative to the teeth to free food debris, bacterial plaque and similar residue from the teeth.

2. Description of the Prior Art

Several patents have been issued on devices which resemble toothpicks in that they are supposedly capable of freeing food debris and the like from a user's teeth. An elongated member having a tapered rounded end, the member being provided with roughened surfaces is shown in U.S. Pat. No. 3,779,256. A resilient elongated device having an irregular configuration is shown in U.S. Pat. No. 3,511,249 and various assemblies of pick-like devices having generally flat configurations and pointed end portions are shown in U.S. Pat. Nos. 2,035,425, 2,760,628 and 3,438,486.

None of the prior art provides a device such as applicant discloses and wherein the body of the device is substantially wide and elongated with corrugations running longitudinally and at least one end curved to form a projecting point into which the corrugations extend. This invention provides a toothpick-like device which may be passed through very narrow areas between the teeth of the user and its corrugated surfaces enable it to engage and hold debris, food particles and the like for faster and better removal from the teeth of the user.

SUMMARY OF THE INVENTION

A toothpick and tooth cleaning device takes the form of an elongated substantially wide section of longitudinally corrugated thin plastic material which is substantially rigid, the opposite ends of which are curved on 90° radii so that a projecting point is defined on one end. Movement of the end portions of the toothpick between the user's teeth readily frees debris, food and dental plaque from between the teeth while the pointed end can be used to push food or other debris from between adjacent teeth.

DESCRIPTION OF THE PREFERRED EMBODIMENT

Figure 1:
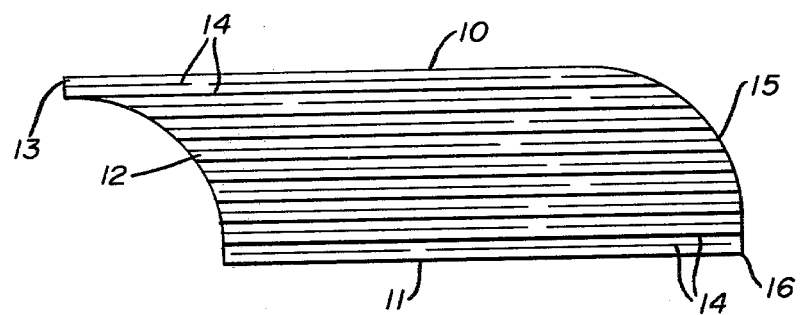
FIG. 1 is a side elevation of the toothpick.

In the drawings of the invention, the toothpick has been considerably enlarged. In actual practice the device is preferably approximately 1 1/16th inches in length and 7/16th inches wide as seen in FIG. 1 of the drawings, and it is preferably formed of rigid but bendable plastic material, such as synthetic resin, which is 0.008 inches thick and corrugated longitudinally so that the actual thickness including the corrugations is 0.016 inches thick.

As seen in FIG. 1 of the drawings, the upper longitudinal edge is indicated at 10, the lower longitudinal edge at 11 and the left end has an arcuate radii or curve 12 which is approximately 90° and which extends from the lower longitudinal edge 11 to a point inwardly from the upper longitudinal edge 10 so as to define a projecting point 13 which is approximately 1/32nd of an inch in width and approximately 0.016 of an inch thick due to the continuation of at least one of several corrugations 14 which extend longitudinally of the toothpick device. The opposite or right end of the device as shown in FIG. 1 is formed with an arcuate curve 15 which is approximately 90° of a circle and extends from the upper longitudinal edge to a point inwardly of the lower longitudinal edge 11 so that a square corner 16 is defined and into the square corner 16 some of the longitudinally extending corrugations 14 extend.

Figure 2:
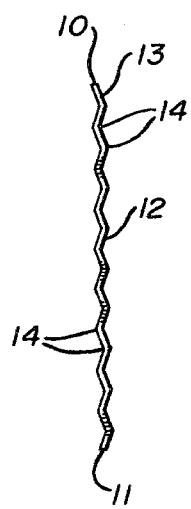
FIG. 2 is an end elevation thereof.

By referring to FIG. 2 of the drawings, which is an end elevation of the left end of the device as seen in FIG. 1, the configuration of the longitudinally extending corrugations 14 may be seen and it will be observed that they are sharply defined having sharp longitudinal fold lines which provide a roughened rasp-like surface on both the front and back sides of the toothpick-like device of the invention.

By referring again to FIG. 1 of the drawings, it will be seen that the toothpick device can be readily grasped between the thumb and the forefinger of the user and used with the projecting point 13 outwardly which can be positioned between the teeth of the user and used to push food particles or other debris therefrom. It will also be observed that due to the curved end 12, the point 13 can be positioned between the teeth and moved substantially therebetween so that a portion of the body of the toothpick-like devices becomes positioned between the teeth to the extent that a number of the corrugations 14 are engaged whereupon movement of the toothpick-like device in a direction corresponding with the direction of the teeth and the space therebetween will cause a rasp-like cleaning of the plaque and other debris from the areas between the teeth. By bending the toothpick-like device while it is so engaged, the areas on the front and back corners of each of the teeth may be also cleaned and by reversing the device and using the other end with its squared corner 16, the wider, flatter portions of the teeth can be similarly engaged so that the food particles, plaque and other debris can be readily removed from the teeth and from the spaces therebetween.

It will thus be seen that the shape of the device and its longitudinally extending sharp line corrugations provides a yieldable tooth engaging device of many widths enabling it to be positioned and moved between the teeth's varying spaces therebetween in a tooth cleaning action.

The hereinbefore described toothpick-like device provides a very inexpensive and highly efficient tooth cleaning article which may be inexpensively formed from sheet plastic material having longitudinally extending corrugations therein by a simple and inexpensive stamping operation. The device is expendible and can be disgarded after each use or alternately it can be washed or otherwise cleaned and reused as desired.

Although but one embodiment of the present invention has been illustrated and described, it will be apparent to those skilled in the art that various changes and modifications may be made therein without departing from the spirit of the invention and having thus described my invention what I claim is:

1. A toothpick comprising an elongated section of thin semi-rigid plastic material, the width of which is approximately one-fourth the length thereof, longitudinally extending closely spaced corrugations formed in said plastic material and at least one end of said toothpick being curved from a point adjacent one of its longitudinal edges to a point inwardly of the opposite longitudinal edges so as to define a projecting point into which at least one of the longitudinal corrugations extends.

2. The toothpick set forth in claim 1 and wherein the thin semi-rigid plastic material is substantially 0.008 of an inch in thickness.

3. The toothpick set forth in claim 1 and wherein the thin semi-rigid plastic material is substantially 0.008 of an inch in thickness and the longitudinally extending closely spaced corrugations formed therein increase the overall thickness thereof to substantially 0.016 of an inch.

4. The toothpick set forth in claim 1 and wherein the other end of said toothpick is curved from a point adjacent one of its longitudinal edges to a point inwardly of the opposite longitudinal edge so as to define a square corner.

5. The toothpick set forth in claim 1 and wherein the plurality of longitudinally extending closely spaced corrugations are defined by relatively sharp fold lines and the peaks and valleys of the plurality of corrugations are spaced with respect to one another by substantially one-sixteeth of an inch.

6. The toothpick set forth in claim 1 and wherein the curved end of the toothpick is formed on a substantial 90° degree radii.

* * * * *